United States Patent [19]
Lowell et al.

[11] Patent Number: 5,961,970
[45] Date of Patent: Oct. 5, 1999

[54] SUBMICRON EMULSIONS AS VACCINE ADJUVANTS

[75] Inventors: George H. Lowell, Baltimore, Md.; Shimon Amselem, Rehovot, Israel; Doron Friedman, Carmei Yosef, Israel; Haim Aviv, Rehovot, Israel

[73] Assignees: Pharmos Corporation, New York, N.Y.; The United States of America as represented by the Secretary of the Army, Washington, D.C.

[21] Appl. No.: 08/637,756

[22] PCT Filed: Oct. 29, 1993

[86] PCT No.: PCT/US93/10402

§ 371 Date: Apr. 29, 1996

§ 102(e) Date: Apr. 29, 1996

[87] PCT Pub. No.: WO95/11700

PCT Pub. Date: May 4, 1995

[51] Int. Cl.[6] .......................... A61K 39/00; A61K 9/127; A61K 9/58; A01N 63/00
[52] U.S. Cl. ................. 424/93.1; 424/184.1; 424/279.1; 424/283.1; 424/455; 424/450; 424/462; 424/278.1; 424/490; 424/452
[58] Field of Search ........................... 424/279.1, 278.1, 424/283.1, 455, 452, 490, 450, 462, 184.1, 93.1

[56] References Cited

U.S. PATENT DOCUMENTS

| | | | |
|---|---|---|---|
| 3,852,155 | 12/1974 | Moore | 195/1.8 |
| 4,073,743 | 2/1978 | Midler, Jr. | 252/309 |
| 4,647,586 | 3/1987 | Mizushima et al. | 514/532 |
| 5,023,271 | 6/1991 | Vigne | 514/458 |
| 5,026,543 | 6/1991 | Rijke | 424/81 |
| 5,171,737 | 12/1992 | Weiner | 514/3 |
| 5,185,146 | 2/1993 | Altenburger | 424/89 |
| 5,188,837 | 2/1993 | Domb | 424/450 |
| 5,284,663 | 2/1994 | Speaker | 424/489 |
| 5,302,401 | 4/1994 | Livesidge | 424/501 |
| 5,306,508 | 4/1994 | Kossovsky | 424/493 |
| 5,308,624 | 5/1994 | Maircent | 424/427 |
| 5,514,670 | 5/1996 | Friedman et al. | |
| 5,576,016 | 11/1996 | Amselem et al. | |
| 5,716,637 | 2/1998 | Amselem et al. | |
| 5,726,292 | 3/1998 | Lowell | |

FOREIGN PATENT DOCUMENTS

| | | |
|---|---|---|
| 0 315 079 | 10/1989 | European Pat. Off. |
| 0399843 | 11/1990 | European Pat. Off. |
| 0 506 197 | 9/1992 | European Pat. Off. |
| 2189143 | 10/1987 | United Kingdom |
| 9014837 | 12/1990 | WIPO |
| 91/07171 | 5/1991 | WIPO |
| WO 92/00081 | 1/1992 | WIPO |
| 9405298 | 3/1994 | WIPO |
| 9511700 | 5/1995 | WIPO |
| 9517159 | 6/1995 | WIPO |
| 9633725 | 10/1996 | WIPO |

OTHER PUBLICATIONS

Journal of Immunological Methods, 135 (1990) 101–109 "Preparation of proteosome–baseed vaccines Correlation of immunogenicity with physical characteristics", by Curtis L. Ruegg et al.

The Journal of Immunology, vol. 140, 1274–1279, No. 4, (1988), "Effective Immunization Against Cutaneous Leishmaniasis With Defined Membrane Antigens Reconsituted Into Liposomes", by David G. Russell.

Analytical Biochemistry 211, 117–122 (1993), "Lyophilized Liposomes as Shelf Items for the Preparation of Immunogenic Liposome–Peptide Conjugates" by M. Friede.

J. Pharm. Pharmacol, (1985), 37: 134–136, "Enhancement of nasal absorption of insulin and clacitonin using polyacrylic acid gel" by Kazuhiro Morimoto.

Pharmaceutical Research, vol. 9, No. 12, 1992, "Mucoadhesion of Copolymers and Mixtures Containing Polyacrylic Acid" by Florence Thermes et al.

Infection and Immunity, Jun. 1993, pp. 2390–2395, "Immunogenicity and Efficicay of Oral or Intranasal Shigella Flexneri 2a and Shigella sonnei Proteosome–Lipopolysaccharide Vaccines in Animal Models" by Nadav Orr et al.

Infection and Immunity, Sep. 1991, pp. 2978–2986, "Biodegradable and Biocompatible Poly(DL–Lactide–Co–Glycolide) Microspheres as an Adjuvant for Staphylococcal enterotoxin B Toxoid Which Enhances the Level of Toxin–Neutralizing Antibodies" by John H. Eldrige et al.

Immunology 1991, 72: 3–9, "Identification and characterization of host–protective T–cell epitopes of a major surface glycoprotein (gp63) from Leishmania major", by D.M. Yang et al.

Journal of Experimental Medicine, vol. 167, 1988, 658–663, "Peptides Bound To Proteosomes Via Hydrophobic Feet Become Highly Immunogenic Without Adjuvants" by George H. Lowell et al.

Biotechnology Therapeutics, 2(1–2__, 91–106 (1990–1991), "Characterization of a Vaccinia–Derived recombinant HIV–1 gp160 Candidate Vaccine and Its Immunogenicity in Chimpanzees" by N. Barrett et al.

CRC Press, Inc., Liposome Technology, 2nd Edition, vol. 1, Chapter 28, p. 501, Liposome Preparation and Related Techniques, edited by Gregory Gregoriadis, Ph.D., "A Large–Scale Method For The Preparation Of Sterile And Nonpyrogenic Liposomal Formulations Of Defined Size Disbributions For Clinical Use", Shimon Amselem, Alberto Gabizon, and Yechezkel Barenholz.

(List continued on next page.)

Primary Examiner—Nita Minnifield
Attorney, Agent, or Firm—Pennie & Edmonds LLP

[57] ABSTRACT

A vaccine adjuvant composition of an oil-in-water submicron emulsion that has about 0.5 to 50% of a first component of an oil, about 0.1 to 10% of a second component of an emulsifier, about 0.05 to 5% of a nonionic surfactant, about 0.00001 to 1% of an immunogen, and an aqueous continuous phase. This submicron emulsion has a mean droplet size in the range of between about 0.03 and 0.5 μm, and preferably 0.05 and 0.2 μm.

25 Claims, 5 Drawing Sheets

OTHER PUBLICATIONS

Methods of Biochemical Analysis, vol. 33, D. Glick, editor, J. Wiley & Sons, N.Y., 1988, "Liposomes: Preparation, Characterization, and Preservation", Dov Lichtenberg and Yechezkel Barenholz.

Journal of Pharmaceutical Sciences, vol. 79, No. 12, Dec. 1990, "optimization and upscaling of Doxorubicin–Containing Liposomes for Clinical Use", S. Amselem, A. Gabizon and Y. Barenholz.

CRC Press Inc., 1993, Liposome Technology 2nd Ed., edited by G. Gregoriadis, PhD., vol. 1, Chapter 3, p. 49, "Liposome Preparation Using High–Pressure Homogenizers", Martin M. Brandl, Dieter Bachmann, Markus Dreschsler, and Kurt H. BauerElsevier Science Publishers B.V. (Biomedical Division, 1986,, Laboratory Technology in Biochemistry and Molecular Biology, vol. 3, part 2, edited by R.H. Burdon and P.H. van knippenberg, "Techniques of Lipidology—Isolation, Analysis and Identification of Lipis", 2nd revision editio, Moris Kates.

Lowell etal, 1996, Infec & Imm. 64(11): 4686–93.

Lowell etal, 1997, J.Infect. Dis. 175: 292–301.

Hagan etal 1997, Mol. Med. Today, Feb. 1997:69–75.

Càjavec etal, 1996, Avian Diseases, 40:193–201.

Kim etal, 1995, J.Immunol., 155:2240–47.

Higgins etal, 1996, Vaccine 14(6):478–484.

Ott etal, 1995, Vaccine, 13(16):1557–1562.

Frankenburg etal, 1996, Vaccine 14(9):923–929.

Hunter etal, 1984, J. Immunol, 133(6):3167–3175.

Yoshioka etal, J. Drug Targeting 2:533–539, 1995.

Hunter etal 1981 J. Immunol. 127(3):1244–1249.

Hagen etal, 1993, Vaccine Research, 2(3):215–225.

Lowell etal, 1988 Science 240:800–802.

☐ 50 μg SEB-Toxiod F + Proteosomes

SUBMICRON EMULSIONS AS VACCINE ADJUVANTS

This application is a 371 of PCT/US93/10402 filed Oct. 29, 1993.

FIELD OF THE INVENTION

This invention relates to the use of oil-in-water submicron emulsions as vaccine adjuvants for enhancing the immunogenicity and improvement of the immune response of antigens and to methods and compositions for preparing them.

BACKGROUND OF THE INVENTION

In the past, the risks of whole-pathogen vaccines and limited supplies of useful antigens posed barriers to development of practical vaccines. Today, the tremendous advances of genetic engineering and the ability to obtain many synthetic recombinant protein antigens derived from parasites, viruses, and bacteria has revolutionized the development of new generation vaccines.

Although the new, small synthetic antigens offer advantages in the selection of antigenic epitopes and safety, a general drawback of small antigens is poor immunogenicity, resulting in low antibody titers and the need for repeated immunizations. This lack of immunogenicity has created an acute need to identify pharmaceutically acceptable delivery systems or adjuvants for these new antigens.

To improve the immune response usually antigens are mixed with adjuvant substances that stimulate immunogenicity. Immunological adjuvants have generally been divided into two basic types: aluminum salts and oil emulsions.

Aluminum phosphate and hydroxide (alum) have a long history of use as adjuvants. They are the only ones recognized as safe for this use by the Food and Drug Administration. Antibody levels against antigens in alum-based vaccines are clearly, although moderately, elevated above those obtained with the corresponding aqueous vaccine. However, aluminum compounds have not always enhanced the immunogenicity of vaccines, and the problem of inconsistent antibody production has been frequently cited. Occasional production of sterile abscesses and persistent nodules were also reported with alum-adjuvanted vaccines. Regarding long term side effects, researchers have suggested a link between aluminum and diseases of the brain, including Alzheimer's disease (Edelman, R.: Vaccine adjuvants. Rev. Inf. Dis. 1980; 2:370–383).

The development of emulsified oil adjuvants emerged historically from the studies of J. Freund who observed a remarkable increase in both the antibody and delayed hypersensitivity response to killed mycobacteria if the organisms were incorporated in paraffin oil. There are two types of Freund's mineral-oil adjuvants: Incomplete Freund's Adjuvant (IFA), consisting of an approximately 50:50 water-in-oil emulsion, and complete Freund's adjuvant (CFA), a similar preparation with inclusion of killed mycobacteria. The powerful antibody-stimulating effect of CFA has not been surpassed by any other adjuvant. However, because of severe pain, abscess formation, fever and granulomatous inflammation, CFA can be used only for experimental purposes and not in human or veterinary vaccines. The toxic reactions reported using mineral oil-adjuvanted vaccines were attributed to impurities in Arlacel A (principally mannide monooleate), the emulsifying agent used in the preparations.

The use of IFA in humans has been limited to those clinical situations in which aqueous vaccines are relatively impotent and aluminum compounds have not provided enough adjuvant activity. J. Salk made practical the use of IFA in human vaccines by using a highly refined mineral oil and a purified Arlacel A emulsifier free of toxic substances injected intramuscularly in thousands of recipients. However, occasional failure of IFA vaccines reported in humans, and the discovery that Arlacel A was carcinogenic in mice, despite the absence of increased tumor formation in humans, has restricted the use of IFA vaccine formulations.

Since CFA was the first successful adjuvant, most investigators followed the example of CFA in assuming that substitutes for each of the three components, viz. oil, emulsifier and immunostimulant, are necessary for formulating a successful adjuvant.

U.S. Pat. Nos. 4,772,466 and 4,606,918 disclose methods for enhancing the immunogenicity of an antigen by emulsifying it with a polyoxypropylene-polyoxyethylene block polymer, a glycol ether-based surfactant, a metabolizable non-toxic oil, and an immunopotentiating amount of an immunostimulating glycopeptide.

Pharmaceutical compositions comprising an oil-in-water micron size emulsion, refined detoxified endotoxin, cell wall skeleton and trehalose dimycolate have been disclosed as vaccine adjuvants in U.S. Pat. Nos. 4,505,900 and 4,803,070.

International patent application (PCT) WO 90/14837 discloses adjuvant composition comprising a metabolizable oil and emulsifying agent in the form of an oil-in-water emulsion, where the antigen is added externally to the prepared emulsion (extrinsic formulation). All the examples in the disclosure contained the immunostimulating agent, MTP-PE, a lipophilic muramyl peptide derivative.

SUMMARY OF INVENTION

The present invention provides vaccine adjuvant compositions in the form of an emulsion of a plurality of submicron oil-in-water droplets having a particle size in the range of between about 30 nm to about 500 nm to effect enhanced immunogenicity of antigens incorporated intrinsically or extrinsically into the droplets. These droplets or particles form a submicron emulsion ("SME") for use as the vaccine adjuvant.

In marked contrast to the aforementioned disclosures, as will be described, the present invention does not require use of any immunostimulatory mycobacteria or muramyl peptide-like additives for its submicron emulsion to be effective. Moreover, as will be seen, a preferred embodiment of the present invention consists of intrinsically incorporating the antigen into the emulsion at the time of formation of the emulsion; this is in distinct contrast to mixing the antigen with the emulsion after the emulsion has been independently extrinsically formed. It will be appreciated that intrinsic formulation will be effective even in situations and conditions and species where extrinsic formulation is not. In this regard as well, the present invention is uniquely different and not at all implied by the previously mentioned applications which indeed teaches away from the present invention in stating that it is sufficient to simply mix the antigen with the extrinsically previously formed emulsion.

The vaccine compositions of this invention also do not include any polyoxypropylene-polyoxyethylene block polymer, trehalose dimycolate, or cell wall skeleton, as are found in prior art compositions.

Another aspect of this invention is to provide compositions and methods for the preparation of submicron emulsions containing antigens, incorporated either intrinsically (emulsified together with the oil and surfactant) or extrinsically (added externally to a prepared SME).

In some cases, the submicron emulsion of the present invention can be administered in combination with other adjuvant systems, such as proteosomes, as indicated in the examples.

The size, concentration and specific formulation of SMEs may be varied to suit the particular antigen used. Moreover, such adjuvant preparations may enhance both humoral and cell-mediated immunity (CMI) as do Freund's adjuvants. The SMEs here described have been developed for human use and since the oily droplets of the emulsions are of submicron size and contain no added pyrogenic moieties such as mycobacteria or MDP derivatives they have, unlike Freund's adjuvants, great safety potential. They may be especially applicable to antigens that are vaccine candidates to protect against biologic toxins or infectious agents, which have natural hydrophobic moieties as a component including transmembrane viral, bacterial or parasite proteins, membrane proteins such as proteosomes, lipopolysaccharides, glycolipids such as gangliosides, or a variety of proteins or peptides to which hydrophobic anchors have been chemically or genetically added.

Another aspect of the invention provides compositions and methods to achieve mucosal immunity by using an emulsion comprising a plurality of submicron particles, a mucoadhesive macromolecule, immunogenic peptide or antigen, and an aqueous continuous phase, which induces mucosal immunity by achieving mucoadhesion of the emulsion particles to mucosal surfaces. Mucous surfaces suitable for application of the emulsions of the present invention may include-ocular (corneal, conjunctival), oral (buccal, sublingual), nasal, vaginal and rectal routes of administration.

The emulsion particles have a hydrophobic core comprising a lipid or lipid-like composition and are stabilized with amphiphilic and/or non-ionic surfactants.

A wide variety of immunogens, including both water-soluble and water-insoluble peptides or polysaccharides, may be accommodated in the present emulsions. The hydrophobic core and surfactant provide a microenvironment which accommodates lipophilic immunogens such as lipid A or lipopolysaccharides as well as membrane-associated peptide antigen domains, while the aqueous continuous phase accommodates water-soluble peptide domains, or oligosaccharides.

The term "peptide" herein includes both oligopeptides and proteins. To facilitate intestinal uptake, the emulsions may be encapsulated in gelatin capsules or otherwise enterocoated to prevent their exposure to gastric fluids when the oral route of administration is selected. Furthermore, the emulsions may be lyophilized as disclosed previously in Pharmos Corp. International Application Publication WO 93/15736 prior to their encapsulation in order to achieve added stability of the antigen.

DETAILED DESCRIPTION OF THE INVENTION

This invention is directed to pharmaceutical compositions comprising submicron emulsions as vaccine adjuvants, and to methods for preparing and using such compositions.

Features of the Submicron Emulsion (SME) Particles

The submicron emulsion vaccine adjuvants of the present invention comprise an aqueous continuous phase suspending a colloidal phase of submicron particles. The particles have a weighted average diameter of about 30 to 500 nm, more preferably about 50 to 200 nm. In many embodiments, the weighted average diameter be less than 460 nm, 400 nm, 300 nm, or 200 nm.

Usually the weighted average diameter will be greater than 40 nm or 50 nm, and frequently is greater than 70 nm. Often, the above-stated upper and lower diameter ranges will include both the weighted average and at least one standard deviation of particle diameter.

The emulsion particle comprises a hydrophobic core, often including or even consisting essentially of a metabolizable and non-toxic oil such as MCT (medium chain triglycerides) oil of the type extensively used in parenteral emulsions like INTRALIPID® or a vegetable oil. Optionally, other hydrophobic lipids may be used, including cholesterol or cholesteryl esters and fatty acids. In many embodiments, the core of the particles will be substantially free of protein other than the antigen to be delivered, i.e. less than 1% (w/w), and in most cases less than 0.1% of other protein.

The emulsion usually further includes at least one surfactant, which may be a natural biologically compatible surfactant such as phospholipid (e.g., lecithin) or a pharmaceutically acceptable non-natural surfactant such as TWEEN-80. The surfactant assists in maintaining particles within the desired size range and preventing their aggregation.

In many embodiments the emulsion may be formed and stabilized in the substantial absence of one or more cosurfactants selected from the group consisting of an unhalogenated aliphatic C3–C6 alcohol, a free fatty acid, a mono- or di-glyceride, a polyglycerol fatty acid ester, or a lysophosphatidyl choline. One or all of the above-named cosurfactants may comprise less than 5%, commonly less than 1%, and frequently less than 0.1% (w/w) relative to the weight of the hydrophobic core.

The emulsion also contains an immunogen, preferably of an antigen. The antigen may be hydrophilic, hydrophobic, or amphiphilic since the emulsion provides a biphasic lipophilic-hydrophilic microenvironment.

The continuous phase of the emulsion is aqueous, and may contain salts, sugars, antioxidants, preservatives, microbicides, buffers, osmoticants, cryoprotectants, and other pharmaceutically useful additives or solutes.

Bioadhesive polymers, such as those currently used in pharmaceutical preparations, optionally may be added to the emulsion to further enhance the immunogenicity through mucous membranes achieving mucosal immunity.

The concentrations indicated by % in the following description denote the concentration by weight of the component per 100 units volume of the entire composition. Also, all indicated concentrations should be understood as standing each by itself, and not cumulative. It should be appreciated by the artisan, however, that there is some dependency between the concentrations of the components, e.g., higher concentrations of the oil will generally require higher concentrations of the emulsifier and surfactant.

The emulsion used in the vaccine compositions of the present invention typically contain about 0.5 to 50% oil, about 0.1 to 10% emulsifier and about 0.05 to 5% of the non-aqueous phase. The combined concentration of the oily and the amphiphilic phase increases viscosity of the composition. In order to obtain a non-viscous composition, the concentration of the non-aqueous phase should generally not exceed about 25%.

Preferred concentrations of the components are as follows: about 1 to 20% oil, most preferably about 1 to 10% for a composition intended to be fluid, about 0.2 to 5% of the emulsifier, with about 0.2 to 5% for the surfactant, with about 0.1 to 2% being particularly preferred.

The antigen is present in an amount of about 0.00001 to 1% by weight of the composition, preferably about 0.0001 to 0.5% and most preferably 0.001 to 0.1%. Depending upon whether the antigen is hydrophilic or hydrophobic, it will be physically present in the oily phase at the oil-water interface, or the aqueous component. Also, the pH of these compositions should be in a range which is suitable for the stability of the antigen.

The submicron emulsion adjuvant formulations of this invention differ from the emulsion adjuvant composition of Patent Application WO 90/14837 in the following features:

(i) all the compositions described in the abovementioned application are prepared extrinsically, namely the antigens are added externally to the previously prepared emulsion by mixing, while in the present invention the antigen can be added either extrinsically or more preferably intrinsically, together with all the emulsion components before emulsification and prior to the mixture of oil and water phases as detailed in the examples; and (ii) all the examples in the abovementioned disclosure contain an immunopotentiating amount of an immune-stimulating glycopeptide of the type of muramyl peptides or their lipophilic derivatives, such as MTP-PE, while in the present invention all the SME adjuvant compositions are prepared in the absence of any muramyl peptide immunostimulating agent.

Composition of the Hydrophobic Core

A hydrophobic compound which is suitably non-toxic may be used as a component of the core. Examples include triglycerides, preferably of food grade purity or better, which may be produced by synthesis or by isolation from natural sources. Natural sources may include animal fat or vegetable oil, e.g., soya oil, a source of long chain triglycerides (LCT). Other triglycerides of interest are composed predominantly of medium length fatty acids, denoted medium chain triglycerides (MCT). A medium chain triglyceride (MCT) oil, is a triglyceride in which the carbohydrate chain has 8–12 carbons. Although MCT oil can be considered as a component of vegetable oil, it is separately identified herein because of its particular utility as a preferred oil for use in the present emulsions. In addition, MCT oil is available commercially. Examples of such MCT oils include TCR (trade name of Societe Industrielle des Oleagineuax, France, for a mixture of triglycerides wherein about 95% of the fatty acid chains have 8 or 10 carbons) and MIGLYOL 812 (trade name of Dynamit Nobel, Sweden for a mixed triester of glycerine and of caprylic and capric acids). The fatty acid moieties of such triglycerides may be unsaturated, monounsaturated or polyunsaturated; mixtures of triglycerides having various fatty acid moieties are acceptable. The core may comprise a single hydrophobic compound or a mixture of compounds.

Examples of vegetable oils include soybean oil, cotton seed oil, olive oil, sesame oil and castor oil. Oily fatty acids, such as oleic acid and linoleic acid, fatty alcohols, such as oleyl alcohol, and fatty esters, such as sorbitan monooleate and sucrose mono-, di- or tripalmitate, can be used as the oil component, although these are not as preferred as the other oils mentioned above.

Optionally, the core may contain cholesterol or cholesteryl esters. In many embodiments, cholesteryl esters or cholesterol comprise less than 10%, 5%, 1%, or even 0.1% (w/w) of the total hydrophobic components of the core. Considerations in choice of core material include low toxicity and irritancy, biocompatibility, safety, metabolizability, stability and high loading capacity for antigens. Preferred hydrophobic core components have molecular weights below about 5,000 Da, more preferably below about 2,000 Da, and most preferably below about 1,500 Da.

Composition of Surfactant Component

The amphiphilic phase comprises the emulsifiers and surfactants. Preferred emulsifiers include a phospholipid compound or a mixture of phospholipids. Suitable components include lecithin; EPICURON 120 (Lucas Meyer, Germany) which is a mixture of about 70% of phosphatidylcholine, 12% phosphatidylethanolamine and about 15% other phospholipids; OVOTHIN 160 (Lucas Meyer, Germany) which is a mixture comprising about 60% phosphatidylcholine, 18% phosphatidylethanolamine and 12% other phospholipids; a purified phospholipid mixture-LIPOID E-75 or LIPOID E-80 (Lipoid, Germany) which is a phospholipid mixture comprising about 80% phosphatidylcholine, 8% phosphatidylethanolamine, 3.6% non-polar lipids and about 2% sphingomyelin. Purified egg yolk phospholipids, soybean oil phospholipids or other purified phospholipid mixtures are useful as this component. This listing is representative and not limiting, as other phospholipid materials which are known to those skilled in the art can be used.

Some embodiments of the invention provide an improved bioadhesive emulsion comprising incorporation of an amphiphilic and/or nonionic surfactant such as phosphatidylcholine, Tween, etc., together with a mucoadhesive polymer macromolecule as described below.

Particularly suitable emulsifiers include phospholipids, which are highly biocompatible. Especially preferable phospholipids are phosphatidylcholines (lecithins), such as soy or egg lecithin. Other suitable phospholipids include phosphatidylglycerol, phosphatidylinositol, phosphatidylserine, phosphatidic acid, cardiolipin, and phosphatidylethanolamine. The phospholipids may be isolated from natural sources or prepared by synthesis. Phospholipid surfactants are believed usually to form a single monolayer coating of the hydrophobic core.

The surfactant is believed in many embodiments to interact with the bioadhesive polymer to form a hydrated polymer film coating associated with the surfactant at the stabilized lipid/water interface surrounding the particle core.

Preferred compositions contain a surfactant component. The surfactant stabilizes the outer surface of the hydrophobic core component of the emulsion particles, thereby promoting a more uniform and manipulatable particle size. Usually the surfactant is present in a proportion of 0.01% to 5% (w/w) of the emulsion, preferably 0.05% to 2% and most preferably 0.1 to 2%.

Typically, the weight percentage of surfactant relative to hydrophobic (oil or other lipid) component is from 0.2% to 50%, more preferably from 5% to 20%. Higher ratios of surfactant to core lipid tend to promote smaller particle core diameters.

Surfactants may be either natural compounds, such as phospholipids and cholates, or non-natural compounds such as: polysorbates, which are fatty acid esters of polyethoxylated sorbitol (TWEEN); polyethylene glycol esters of fatty acids from sources such as castor oil (EMULFOR); polyethoxylated fatty acid, e.g., stearic acid (SIMULSOL M-53); NONIDET; polyethoxylated isooctylphenol/formaldehyde polymer (TYLOXAPOL); polyoxyethylene fatty alcohol ethers (BRIJ); polyoxyethylene nonphenyl ethers (TRITON N); polyoxyethylene isooctylphenyl ethers (TRITON X). Mixtures of surfactant molecules, including mixtures of surfactants of different chemical types, are acceptable. Surfactants should be suitable for pharmaceutical administration and compatible with the peptide to be delivered.

In certain embodiments, the emulsion may be limited in or substantially free of one or more cosurfactants selected from the group consisting of free fatty acids, mono- or diglycerides (fatty acid mono- or diesters of glycerol), aliphatic C3–C6 monoalcohols (exclusive of, e.g., chlorobutanol or other haloalkyl alcohol preservative), polyglycerol fatty acid esters, or lysophosphatidyl choline. In many embodiments, the particular limited cosurfactant from the above group may constitute less than 5%, usually less than 1%, often less than 0.1%, relative to the weight of hydrophobic core component. In some embodiments, one or more cosurfactants may be present.

Continuous Aqueous Phase

The aqueous component will be the continuous phase of the emulsion and may be water, saline or any other suitable aqueous solution which can yield an isotonic and pH controlled preparation.

In addition, the compositions of the invention may also comprise conventional additives such as preservatives, osmotic agents or pressure regulators and antioxidants. Typical preservatives include Thimerosal, chlorbutanol, and methyl, ethyl, propyl or butyl parabens. Typical osmotic pressure regulators include glycerol and mannitol, with glycerol being preferred. The preferred oil phase antioxidant is α-tocopherol or α-tocopherol succinate. The aqueous phase may also include an antioxidant of a polyamine carboxylic acid such as ethylene diamino tetraacetic acid, or a pharmaceutically acceptable salt thereof.

Antigens

Since the SME particles provide a hydrophilic-lipophilic microenvironment, either water-soluble or lipid-soluble immunogens can be incorporated in the SME vaccines of the present invention. Examples of peptide antigens are: hydrophilic natural or synthetic peptides and proteins derived from bacteria, viruses and parasites, such as the recombinant gp160 envelope protein of the HIV virus; natural or synthetic glycoproteins derived from parasites, bacteria or viruses such as the native surface glycoprotein of Leishmania strain or subunit vaccines containing part of the glycopeptides alone or covalently conjugated to lipopeptides like lauryl-cystein hydrophobic foot; protein toxoids such as the Staphylococcus enterotoxin B toxoid, either chemically or physically inactivated, non-toxic bacterial surface structures (fimbrial adhesions) of *Eschesichia coli* strains such as the Shiga-like Toxin B Subunit (SLT-B) and AF-RL, a pilus adhesion which is a virulence factor for RDEC-1 *E. coli* strain; outer membrane proteins of *Neisseria meningitides;* Hepatitis B surface antigen; native or synthetic malaria antigens derived from different portions of *Plasmodium falciparum,* etc.

Examples of lipophilic or hydrophobic immunogens are lipopolysaccharides (LPS), such as detoxified LPS obtained from *E. coli* (Sigma Chemical Co., St. Louis, USA); Lipid A, the terminal portion of LPS, such as the one isolated from Salmonella minnesota R595 from List Biological Laboratories (CA, USA).

In some embodiments, the emulsion particles will be free or substantially free of the above or other nonbioactive proteins, i.e. less than 5%, usually less than 1%, and frequently less than 0.1% (w/w) protein relative to other particle components.

Bioadhesive SME Vaccine Adjuvants

Submicron emulsion vaccine adjuvants of the present invention optionally may contain a bioadhesive macromolecule or polymer in an amount sufficient to confer bioadhesive properties. The bioadhesive macromolecule enhances the delivery and attachment of antigens on or through the target mucous surface conferring mucosal immunity. The bioadhesive macromolecule may be selected from acidic non-naturally occurring polymers, preferably having at least one acidic group per four repeating or monomeric subunit moieties, such as polyacrylic acid and/or polymethacrylic acid (e.g. CARBOPOL, CARBOMER), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl) methylcellulose; basic amine-bearing polymers such as chitosan; acidic polymers obtainable from natural sources, such as alginic acid, hyaluronic acid, pectin, gum tragacanth, and karaya gum; and neutral non-naturally occurring polymers, such as polyvinylalcohol; or their mixtures.

The ionizable polymers may be present as free acids, bases, or salts, usually in a final concentration of 0.01–0.5% (w/v).

As used herein, a polymer of an indicated monomeric subunit contains at least 75%, preferably at least 90%, and up to 100% of the indicated type of monomer subunit; a copolymer of an indicated type of monomeric subunit contains at least 10%, preferably at least 25% of that monomeric subunit.

A preferred bioadhesive macromolecule is the family of acrylic acid polymers and copolymers (e.g. CARBOPOL™). These contain the general structure:

$$-[-CH_2-CH(COOH)-]-n$$

One preferred group of polymers of acrylic acid is commercially available under the tradename CARBOPOL. CARBOPOL 934 is available in a pharmaceutical grade.

Preferred bioadhesive or mucoadhesive macromolecules have a molecular weight of at least 50 kDa, preferably at least 300 kDa, and most preferably at least 1,000 kDa. Favored polymeric ionizable mucoadhesive macromolecules have not less than 2 mole percent acidic groups (e.g. COOH, $SO_3H$) or basic groups ($NH_2$, NRH, $NR_2$), relative to the number of monomeric units. More preferably, the acidic or basic groups constitute at least 5 mole percent, more preferably 25 or even 50, up to 100 mole % relative to the number of monomeric units of the macromolecule.

Preferred macromolecules also are soluble in water throughout their relevant concentration range (0.01–0.5% w/v).

Methods of Preparation

A further embodiment of the invention relates to methods for preparation of submicron emulsion vaccine adjuvants intrinsically and extrinsically as extensively detailed in the examples. In general, SME intrinsic formulations are prepared by emulsifying the antigen together with the SME components, while SME extrinsic formulations are prepared by adding externally the antigen to previously prepared plain SME.

Dehydrated SME Adjuvants

A further aspect of the invention provides dehydrated emulsions, made by dehydrating the submicron emulsion of the types described herein. Dehydrated submicron emulsions may be stored for prolonged periods with minimal degradation, then reconstituted with water shortly before use. Residual water content in the dehydrated emulsion is usually less than 5% (w/w), commonly less than 2%, and often less than 1%.

Dehydration may be performed by standard methods, such as drying under reduced pressure; when the emulsion is frozen prior to dehydration, this low pressure evaporation is known as lyophilization. Freezing may be performed conveniently in a dry ice-acetone or ethyl alcohol bath. The pressure reduction may be achieved conveniently with a mechanical vacuum pump, usually fitted with a liquid nitrogen cold trap to protect the pump from contamination. Pressures in the low millitorr range, e.g., 10–50 millitorr, are routinely achievable but higher or lower pressures are sufficient.

A cryoprotectant or anticoalescent compound may be added to the emulsion prior to dehydration to inhibit flocculation and coalescence upon rehydration. The cryoprotectant may be of any type known in the art, including sugars and polysaccharides such as sucrose or trehalose, and non-natural polymers such as polyvinylpyrrolidone. Cryoprotectants are usually present at less than 25%, commonly 10%, more commonly 5%, 4% (w/v) or less in the emulsion before lyophilization.

A preferred category of cryoprotectants is amino acids and oligopeptides. Preferred amino acids include valine, leucine, isoleucine, lysine, methionine, threonine, serine, arginine, alanine, glycine, histidine, proline, phenylalanine, taurine, and carnitine, although any of the other natural amino acids may also be present. Amino acids may be of either D or L configuration, or a mixture; the natural L form is preferred. Amino acids may be present as their salts or esters, and as mixtures of amino acids or as pure species.

A particularly preferred amino acid is glycine, which may be present either in pure form or as a component of a mixture, e.g. in an hydrolyzate of collagen or other glycine-rich protein.

Mixtures of oligopeptides, especially di- and tripeptides, are another preferred type of cryoprotectant. These may be prepared conveniently as partial protein hydrolysates or enzymatic digests.

The cryoprotective amino acids or oligopeptides are generally present in the emulsion at a concentration of about 0.25 to 25% (w/w), preferably about 0.5 to 12% (w/w), more preferably about 1 to 10% (w/w) and commonly 3–6% (w/w).

Cryoprotectants and methods of making lyophilized submicron emulsions are taught in more detail in Pharmos Corp. PCT International Application Publication WO 93/15736 entitled "Dry Compositions for Preparing Submicron Emulsions", the content of which is expressly incorporated herein by reference.

EXAMPLES

This invention is illustrated by the following non-limiting examples:

Example 1

Preparation of Intrinsic-gp160-SME vaccine

Antigen Description and Background

The urgency and high priority for developing an effective vaccine against the human immunodeficiency virus (HIV) are fully recognized. The reasons for using subunits of the virus as the basis of an HIV vaccine are the perceived overwhelming requirements for safety. Despite the high efficacy of many live attenuated viral vaccines, the requirement for product safety, especially in the case of retroviruses, has favored the subunit approach to the extent that all of the current candidate preparations in clinical prophylactic trials are of this type, being mainly gp160, the envelope protein of HIV, or part thereof. Studies have shown that gp160 attaches the virus to the cell and also facilitates the fusion of the cell and virus during the early stages of infection.

The gp160 antigen used in this example was supplied by MicroGeneSys Inc. This gp160 recombinant protein in alum-adjuvanted vaccine formulation is currently under evaluation in human clinical trials.

Preparation of Oil Phase

The oil phase was composed of MCT oil (2.0 g Mygliol 812, Hulls, Germany), lecithin (0.4 g, Lipoid E-80, Germany), and DL-α-tocopherol succinate (8.0 mg, Merck, Germany). The lipids and oil were weighed in a 250-ml beaker and mixed at room temperature using a magnetic stirrer during 2–4 hrs until a homogenous and almost clear solution was obtained.

Preparation of Water Phase

Polysorbate 80 (1% w/v, Montanox 80, DF, Seppic, France), Glycerol (2.2% w/v, Merck, Germany), EDTA (0.1% w/v, Merck, Germany), and purified water (to 100% w/v) were dissolved at room temperature in a 250-ml beaker by gentle shaking using a magnetic stirrer plate until a clear homogenous solution was obtained (about 15–20 min). A total volume of 40 ml of water phase was prepared. A vial containing 2.1 ml of gp160 recombinant protein (MicroGeneSys, Inc., CT, USA) at a concentration of 0.25 mg/ml in saline was added to the water phase and the mixture was gently shaken for 5 min.

Mixing of Oil and Water Phase

The oil phase was heated to 40° C. and added to the beaker containing the 40 ml of water phase. The mixture was gently stirred for 10–15 min at room temperature.

Preparation of Oil-in-Water Coarse Emulsion

An oil-in-water emulsion containing the antigen was prepared using the medium-sized disperser and homogenizing unit Polytron PT3000 (Kinematics, Switzerland) at 3,600 rpm for 30 sec. The resultant micronsize emulsion was cooled at room temperature.

Sizing of Emulsion to Submicron Range

The droplet size of the emulsion obtained after Polytron step was lowered to the submicron (nanosize) range by submitting the emulsion to high shear homogenization using the Gaulin Microlab 70 High Pressure Homogenizer (APV Gaulin, Germany) at 800 bar pressure. A total of 10 cycles were performed. The particle size distribution of the resultant formulation was determined using an N4MD Coulter Particle Size Analyzer (Coulter Electronics, England). The differential weight % mode of the instrument indicated the existence of homogeneous population of SME droplets with a mean particle size distribution of 43±35 nm. The estimated final gp160 concentration in the formulation was 56 µg/ml.

Example 2

Preparation of Intrinsic-SME Vaccine Containing gp160 Complexed to Proteosomes Proteosomes are meningococcal outer membrane protein reparations purified from *Neisseria meningitidis* by detergent extraction and ammonium sulphate precipitation. They naturally form 20–100 nm diameter hydrophobic membraneous vesicles. Antigens are non-covalently complexed to proteosomes via hydrophobic interactions by mixing the antigen and proteosomes in the presence of detergent and then removing the detergent over a prescribed period of time, permitting hydrophobic interactions to occur in the system.

Proteosomes have previously been shown to enhance the parenteral immunogenicity of peptides, gangliosides, lipopolysaccharides and proteins hydrophobically complexed to them (Lowell, G. H., L. F. Smith, R. C. Seid and W. D. Zollinger, J. Exp. Med. 167: 658–663, 1988). (Lowell, G. H., W. R. Ballou, L. F. Smith, R. A. Wirtz, W. D. Zollinger and W. T. Hockmeyer. Science 240: 800–802, 1988; Lowell, G. H. 1990. In: New Generation Vaccines. G. C. Woodrow and M. M. Levine (eds.), Marcel Dekker, Inc., New York, p. 141–160). and have been shown to be safe for human use in vaccine trials involving tens of thousands of humans in the development of anti-meningococcal vaccines (Zollinger, W. D. New and Improved Vaccines Against Meningococcal Disease. In: New Generation Vaccines, G. C. Woodrow and M. M. Levine (eds.), Marcel Dekker, Inc., New York, p. 325–348). Furthermore, proteosomes confer mucosal immunogenicity upon non-immunogenic antigens when administered orally or intranasally. Such intranasal or oral proteosome vaccines induce up to 100% protection against lethal pneumonia or keratoconjunctivitis in experimental murine models of shigellosis (Orr, N., G. Robin, D. Cohen, R. Arnon and G. Lowell. 1993. Immunogenicity and efficacy of oral or intranasal *Shigella flexneri* 2a and *Shigella sonnei* proteosome-lipopolysaccharide vaccines in animal models. Infect. Immun. 61: 2390–2395).

Oil and aqueous phases were prepared as described in Example 1. A vial containing 2.5 mg of gp160 non-covalently complexed to proteosomes and suspended in saline was added to the water phase (40 ml total volume) and the mixture was gently shaken for 5 min. The subsequent steps involved in the preparation of the SME, i.e. mixing of oil and water phases, homogenization and sizing to submicron range were carried out as described in Example 1. The particle size volume % distribution of the resultant formulation showed a mean droplet size of 38±41 nm. The estimated final gp160 concentration in the formulation was 46 µg/ml.

Example 3

Preparation of Extrinsic-gp160-SME Vaccine

Extrinsic formulations of gp160 in SME were performed by preparing plain SME as described in Example 1, but in the absence of the antigen and adding externally the aqueous solution containing the gp160 to the plain SME by gently shaking for 15 min at room temperature. A total volume of 2.3 mi of plain SME (average droplet size of 50±36 nm) were mixed with 2.1 ml solution of gp160 in saline containing 1.1 mg protein to give a final gp160 concentration of 0.25 mg/ml.

Example 4

Preparation of Extrinsic-SME Vaccine Containing gp160 Complexed to Proteosomes Extrinsic formulation of gp160 conjugated to proteosomes in SME were performed by preparing plain SME as described in Example 1, but in the absence of the antigen and adding externally an aqueous dispersion of the gp160-conjugated to proteosomes to the plain SME by gently shaking for 15 min at room temperature. A total volume of 5.4 ml of plain SME (average droplet size of 50±36 nm) were mixed with 7.0 ml saline containing 3.1 mg of gpl 60 complexed to proteosomes to give a final gp160 concentration of 0.25 mg/ml.

Example 5

Preparation of Intrinsic-SME Vaccine Containing Staphylococcus Enterotoxin B Toxoid-F Antigen description and background: Staphylococcal enterotoxin B (SEB) is a potent toxin that causes food borne illness among civilians and military personnel stationed around the world and is identified as a lethal offensive military threat that endangers both military and civilian populations through aerosolization.

SEB infection in civilian populations is related to staphylococcal food poisoning by SEB and related toxins: also contributes to death from staphylococcal sepsis following overwhelming staph infection. It also causes staph scalded skin syndrome in kids—i.e. morbidity and mortality from staphylococcal infections (P. Marrack and J. Kappler, Science, vol. 248, pp. 705–711.)

Due to the similarity to the human response both in sensitivity and clinical signs and the lack of an established model for lethality to SEB delivered via the respiratory route in lower animal species, non-human primates have been the primary animal model for development of vaccines to protect against respiratory challenge with SEB. Early work indicated that monkeys develop decreased sensitivity to repeated mucosal administration of the toxin. This suggested that protection to SEB exposure might be provided by toxoid immunization. Studies in rhesus monkeys and other animals indicated that oral immunization with formalinized toxoid was ineffective against parenteral challenge whereas parenteral immunization with formalinized SEB toxic induced serum antibodies that recognized native SEB (Bergdoll, M. S. Enterotoxins. pp. 559–598 In: Staphylococci and Staphylococcal Infections, eds. C. S. F. Easmon and C. Adlam, Academic Press, London, 1983). In the latter studies, however, several parenterally immunized monkeys that acquired anti-SEB antibodies had severe immediate-type hypersensitivity reactions when challenged with SEB toxin. These adverse reactions suggested that the formalinized SEB toxoid alone was not a candidate for parenteral vaccine development. Additionally, as the military threat would be by aerosolization, it was determined that studies on protection provided by serum IgG to respiratory challenge as well as protective effects provided by anti-SEB secretory IgA in the respiratory tract were required.

Recently, two identical lots of formalinized SEB toxoid were made at Walter Reed Army Institute of Research, Washington DC (WRAIR) following previously described specifications (Kaminski, R., S. Grate, E. Aboud-Pirak, C. Hooper, T. Levin, I. Weiss, S. Amselem, R. Arnon and G. Lowell, 1993). Comparison of induction of respiratory IgA and serum lg by intranasal and parenteral proteosome vaccines formulated with staphylococcal enterotoxin B toxoids or ricin peptides. In Proceedings of 1993 Medical Defense Bioscience Review, Baltimore, Md.). This WRAIR formalinized toxoid preparation designated Tox-F was non-toxic in rabbits at 0.5 mg/kg, the dose at which SEB toxin is invariably lethal. Furthermore, it was non-toxic in the murine D-galactosamine model of SEB toxicity even at 500 μg per BALB/C mouse; 50 μg of SEB is 100% lethal in such mice. The physical characteristics of Tox-F were similar to that described by Eldridge (Eldridge, J. H., Staas, J. K., Meulbroek, J. A., Tice, T. T. and Gilley, R. M. Biodegradable and biocompatible poly(DL-lactide-co-glycolide) microspheres as an adjuvant for staphylococcal enterotoxin B toxoid which enhances the level of toxin-neutralizing antibodies. Infect. Immun. 59: 2978–2986, 1991) is that SDS-PAGE gel of Tox-F showed two distinct bands with estimated MW of 23,000 and 46,000. Biologically, Tox-F also had the characteristics previously reported by Eldridge et al., namely in a Mouse Spleen Lymphocyte Proliferative Assay in which concentrations of SEB toxin of 0.37–10.0 μg/ml were mitogenic, Tox-F was entirely non-mitogenic at all concentrations tested (0.04–1 00.0 μg/ml).

Preparation of SEB-Toxoid F

Formalinized SEB-Toxoid (Tox-F) was prepared according to the method of Warren, J. R., Spero, L. and Metzger, J. F. 1983. J. Immunol. 111: 885–892 and as per Eldridge, J. H. et al. 1991, Infect. Immun. 59: 2978–2986 by formalin treatment for 30 days at 37° C., pH 7.5.

Preparation of SME

Preparation of oil phase

Oil phase was composed of MCT oil (0.77 g, Mygliol 812, Hulls, Germany), lecithin (0.14 g, Lipoid E-80, Germany) and DL-α-tocopherol succinate (9.0 mg, Merck, Germany). The lipids and oil were weighed in a 250-ml beaker and mixed at room temperature using a magnetic stirrer during 2–4 hours until a homogenous and almost clear solution was obtained.

Preparation of Water Phase

Polysorbate 80 (0.5% w/v, Montanox 80, DF, Seppic, France), Glycerol (2.2% w/v, Merck, Germany), EDTA (0.1% w/v, Merck, Germany), and purified water (to 100% w/v) were dissolved at room temperature in a 250-ml beaker by gently shaking using a magnetic stirrer plate until a clear homogenous solution was obtained (about 15–20 min). A total volume of 45 ml of water phase was prepared. A vial containing 10 ml of SEB-Toxoid F in 6.3 ml buffer was added to the water phase and the mixture was gently shaken for 5 min.

Preparation of Oil-in-Water Coarse Emulsion

An oil-in-water emulsion containing the antigen was prepared by heating the oil phase to 40° C. and mixing it with the water phase with the aid of a 10 ml glass pipette until a homogenous and milky dispersion was obtained. The resultant micronsize emulsion was cooled at room temperature.

Sizing of Emulsion to Submicron Range

Figure 1:
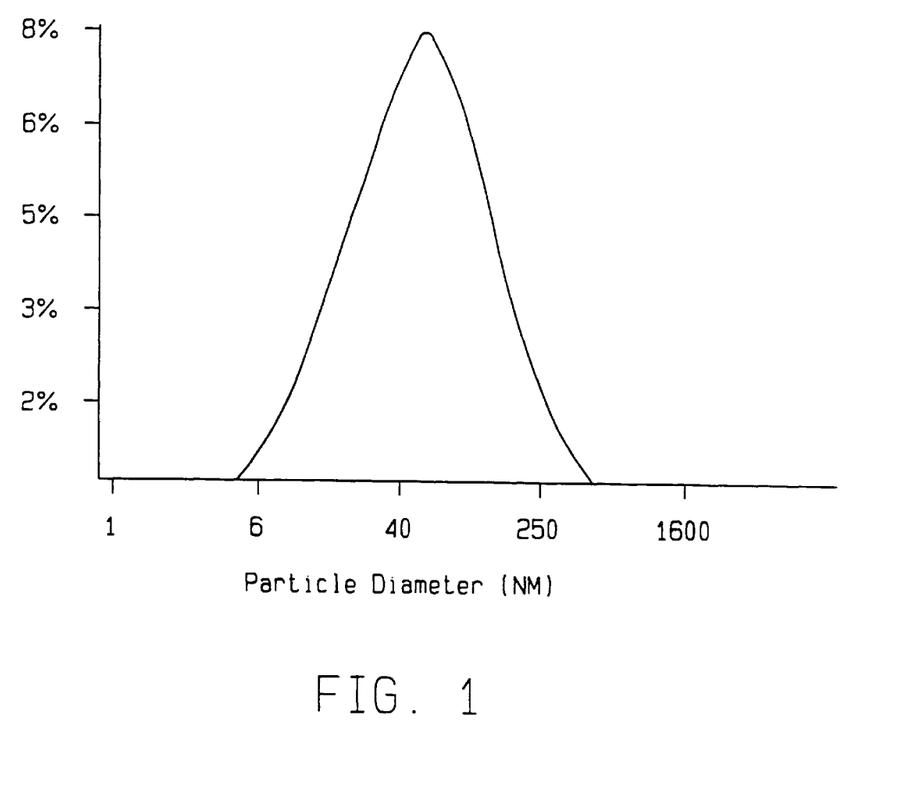
FIG. 1 is a graph showing the size distribution of Intrinsic-SME vaccine containing SEB-Toxoid F antigen.

The droplet size of the emulsion obtained after the Polytron step was lowered to submicron (nanosize) range by subjecting the emulsion to high shear homogenization using the Gaulin Microlab 70 High Pressure Homogenizer (APV Gaulin, Germany) at 800 bar pressure. A total of 5 cycles were performed. The particle size distribution of the resultant formulation was determined using an N4MD Coulter Particle Size Analyzer (Coulter Electronics, England). The differential weight % mode of the instrument indicated the existence of a single and homogenous population of SME droplets with a mean particle size distribution of 47.5±58 nm (see FIG. 1). The estimated final antigen concentration in the formulation was 220 μg/ml.

Example 6

Preparation of Extrinsic SME Vaccine Containing Staphylococcus Enterotoxin B Toxoid-F Extrinsic formulations of SEB-Toxoid-F in SME were performed by preparing plain SME as described in Example 5, but in the absence of the antigen and adding externally the aqueous solution containing the SEB-Toxoid-F to the plain SME by gently shaking for 15 min at room temperature. A total volume of 0.780 ml of stock SME were mixed with 0.780 ml solution of SEB-Toxoid-Fin 0.01 M Tris 0.15M NaCl buffer containing 0.780 mg protein to give a final SEB-Toxoid-F concentration of 0.500 mg/ml.

Example 7

Preparation of Extrinsic SME Vaccine Containing Staphylococcus Enterotoxin B Toxoid P Complexed to Proteosomes Extrinsic formulations of SEB-Toxoid-F in SME were performed by preparing plain SME as described in Example 5, but in the absence of the antigen and adding externally the aqueous solution containing the SEB-Toxoid-F complexed to proteosomes to the plain SME by gently shaking for 15 min at room temperature. A total volume of 0.780 ml of stock SME were mixed with 0.780 ml solution of SEB-Toxoid-F complexed to proteosomes in 0.01 M Tris 0.15M NaCl buffer containing 0.780 mg protein to give a final SEB-Toxoid-F concentration of 0.500 mg/ml.

Example 8

Preparation of Extrinsic-SME Vaccine Containing Staphylococcus Enterotoxin B Toxoid C Preparation of SEB-Toxoid-C Carboxymethylated Toxoid (Tox-C): Carboxymethylated with 0.4 Bromoacetic Acid, pH 7.0 for 11 or 21 days in the dark at 20° C. as per Stema, G. N. and Bergdoll, M. S. 1982. Biophys. Biochem. Res. Commun. 105: 121–126 and as per Scheuber et al. 1985. Infect. Immunol. 50: 869–876. Made at WRAIR according to described methods.

Extrinsic formulations of SEB-Toxoid-C in SME were performed by preparing plain SME as described in Example 5, but in the absence of the antigen and adding externally the aqueous solution containing the SEB-Toxoid-C to the plain SME by gently shaking for 15 min at room temperature. A total volume of 0.165 ml of stock SME were mixed with 0.110 ml solution of SEB-Toxoid-C in water containing 0.110 mg protein to give a final SEB-Toxoid-C concentration of 0.400 mg/ml.

Example 9

Preparation of Extrinsic SME Vaccine Containing Staphylococcus Enterotoxin B Toxoid-C Complexed to Proteosomes Extrinsic formulations of SEB-Toxoid-C in SME were performed by preparing plain SME as described in Example 5, but in the absence of the antigen and adding externally the aqueous solution containing the SEB-Toxoid-C complexed to proteosomes to the plain SME by gentle shaking for 15 min at room temperature. A total volume of 0.045 ml of stock SME were mixed with 0.230 ml solution of SEB- Toxoid-C complexed to proteosomes in water containing 0.110 mg protein to give a final SEB-Toxoid-C concentration of 0.400 mg/ml.

Example 10

Preparation of Mucoadhesive Extrinsic SME Formulation Containing 0.05% Carbopol 420 ml of distilled water in which were dissolved 0.250 g Carbopol-940 (Goodrich, U.S.) and 11.2 g glycerol (isotonic agent), pH 3.82, were warmed to 45° C. and mixed with the oil phase, consisting of 21.2 g MCT oil (medium chain triglycerides, SIO, France), 3.74 g Lipoid E-75 (egg lecithin) and 1.5% w/v Emulfor EL-620 (Rhone-Poulenc, France), at a temperature of 60° C. After mixing by high speed stirrer (Polytron 3000, Kinematica, Switzerland) at 20,000 rpm for 5 minutes the mixture was dispersed by a high pressure homogenizer (Gaulin Microlab 70) at 700 bar for 5 minutes (approximately 10 cycles). The resulting emulsion was cooled, and after adjusting the pH to 5.0, the emulsion was filtered and packed in sterile bottles through a 0.2 $\mu$m filter.

After filtering, droplet size was measured by the photon correlation spectroscopy using a particle size analyzer (N4MD, Coulter Electronics, U.S.A.). The droplet size for carbopol containing droplets was 127±79 nm. This mucoadhesive composition was prepared as an extrinsic plain SME formulation to be added to the specific immunogen by gentle mixing.

Example 11

Figure 2A:
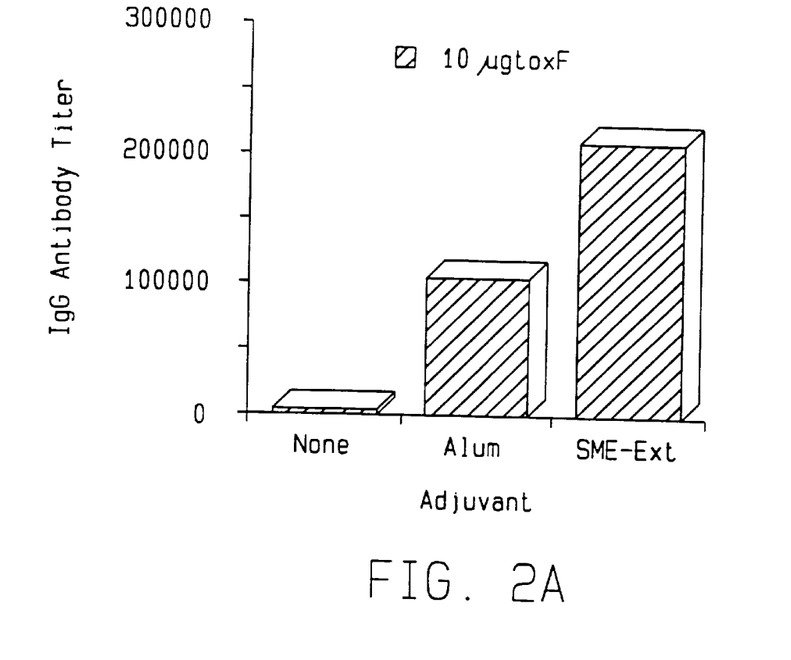
FIGS. 2A and 2B show the immune response obtained after parenteral immunization with formalinized SEB-Toxoid (Toxoid F) at two different antigen doses, 10 μg (A) and 50 μg (B), formulated in extrinsic-SME, intrinsic-SME, alum, or free antigen.
Figure 2B:
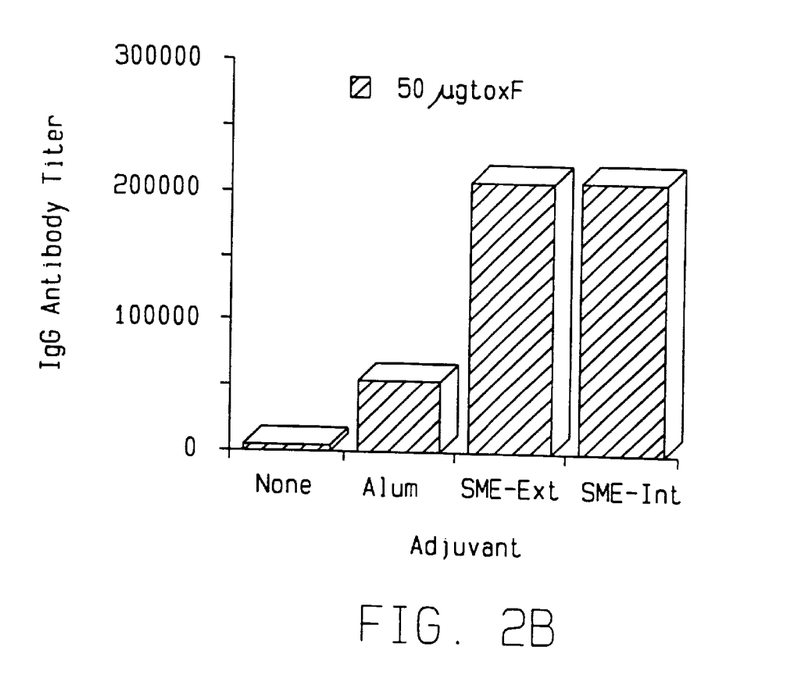
Figure 3:
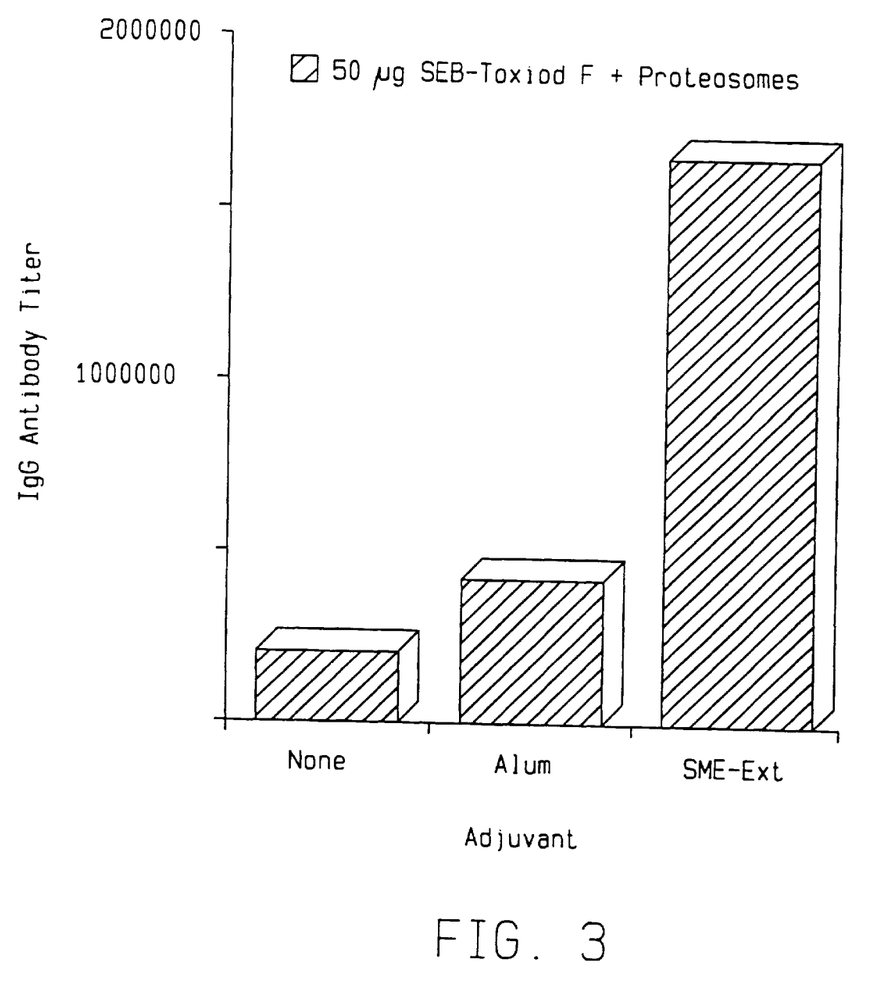
FIG. 3 shows the immunogenicity of SEB-Toxoid F complexed to proteosomes as a free antigen or adjuvanted with alum or extrinsic SME.

Enhanced Immunogencity to SEB Antigen after Parenteral Immunization with Intrinsic and Extrinsic SEB-Toxoid F-SME Vaccines Compared to Free Antigen or Alum-Adjuvanted Vaccine The antigen used was Staphylococcal Enterotoxin B (SEB) toxoid F alone or SEB toxoid complexed to meningococcal outer membrane proteosomes. This antigen was formulated with SME adjuvant either intrinsically or extrinsically, as described in Examples 5, 6 and 7, and compared to SEB toxoid-F alone or adjuvanted with alum. Outbred CD-1 mice, 5 animals/group, were immunized twice at approximately 3 week intervals by intramuscular injections with 10 or 50 $\mu$g doses of SEB Toxoid F. Sera, obtained after first and second immunizations, were analyzed by ELISA techniques using anti-SEB as the detecting antibody. As shown in FIGS. 2 and 3, intrinsic and extrinsic-SME formulations with (FIG. 2) or without proteosomes (FIG. 3) were effective in enhancing immunity to SEB antigens. In all the cases, the anti-SEB serum IgG titers obtained with the SME-adjuvant were several orders of magnitude higher than those obtained with the alum-adjuvanted formulation.

Example 12

Enhanced Immunogenicity to SEB Antigen after Parenteral Immunization with SEB-Toxoid-C SME Vaccines Compared to Free Antigen or Alum-Adjuvanted Vaccine The antigen used was carboxymethylated SEB-Toxoid or Toxoid-C. The antigen was incorporated extrinsically in SME, as described in Example 9. The immunization protocol and sera analysis for antibody activity was as described in Example 11. Mice were immunized intramuscularly with two 10 $\mu$g doses of Toxoid-C. As shown in Table 1, parenteral immunization with Toxoid-C-SME vaccine induced a 4-fold increase in the level of serum IgG even in the absence of proteosomes.

TABLE 1

Effects of formulation with saline, alum or submicron emulsion (SME) on parenteral (intramuscular) immunogenicity of carboxymethylated SEB toxoid (Toxoid-C)

| Antigen (2 doses) | Adjuvant | Anti-SEB serum IgG titer (OD > 0.5 at 1 hr) |
|---|---|---|
| SEB Toxoid-C | None (saline) | 819,200 |
| SEB Toxoid-C | Alum | 6,553,600 |
| SEB Toxoid-C | SME | 3,276,800 |

Example 13

Intranasal Immunization with SEB-Toxoid F SME Vaccines

Immunization against biologic threat agents, such as SEB requires the development of vaccines that can protect against respiratory challenge. The induction of respiratory IgA as well as serum IgG is likely to be critically important to the success of such vaccines. To elicit effective respiratory, as well as systemic, immunity it may be necessary to develop a vaccine system that can be delivered intranasally, as well as parenterally.

BALB/c mice (8 animals/group) were immunized twice by intranasal slow dropwise instillation into both nostrils with SEB-Toxoid F (10 $\mu$g doses) formulated with or without proteosomes as a free antigen or adjuvanted with SME. Immunogenicity of these formulations was evaluated after the two immunizations by determining systemic IgG antibody activity against SEB and induction of anti-SEB respiratory IgA antibody titers.

As shown in Table 2, Toxoid-F formulated in extrinsic SME either with or without proteosomes conferred intranasal immunogenicity resulting in 500- to 2000-fold enhancement of anti-SEB serum IgG antibody activity.

TABLE 2

Effects of formulation of formalized SEB (Toxoid-F) with submicron emulsion (SME) and/or proteosomes on induction of anti-SEB serum IgG following intranasal immunization

| Antigen (2 doses) | Adjuvant | Anti-SEB serum IgG titers (O.D. > 0.5 at 1 hr) | |
|---|---|---|---|
| | | w/o protoeosomes | formulated with proteosomes |
| SEB Toxoid-F | None (saline) | 100 | 51,200 |
| SEB Toxoid-F | SME | 51,200 | 204,800 |

Extrinsic SME formation of Toxoid-F complexed to proteosomes also enhanced lung IgA antibody levels to SEB (Table 3).

TABLE 3

Enhanced production of anti-seb respiratory (lung) IgA antibodies after intranasal immunization of BALB/c mice with 10 μg SEB-Toxoid F antigen alone or adjuvanted with SME

| Antigen | Adjuvant | Anti-SEB lung IgA titer |
|---|---|---|
| SEBtox-F | None (saline) | 0 |
| SEBtox-F | Extrinsic SME | 0 |
| SEBtox-F | Intrinsic SME | 0 |
| SEBtox-F-proteosomes | None (saline) | 0.6 |
| SEBtox-F-proteosomes | Extrinsic SME | 10 |

Example 14

Intranasal Immunization with Lipopolysaccharide (LPS) Antigen from S. flex Complexed to Proteosomes Adjuvanted with Extrinsic-SME Evidence that the SME has potential as a mucosal adjuvant is also shown by the ability of the extrinsic-SME adjuvant formulation to markedly enhance the lung IgA of the proteosome-LPS antigen when given intranasally (Table 4) compared to the free antigen. The immunization protocol included two groups of BALB/c mice (4 animals each) which were immunized intranasally with 10 μg does of LPS from S. flex compared to proteosomes. The non-covalent complexation of LPS to proteosomes was carried out in a similar way as described in Example 2.

TABLE 4

Induction of mucosal immunity after intranasal immunization of Balb/C mice with 10 μg LPS-complexed to proteosomes as a free antigen or adjuvanted with extrinsic-SME

| Antigen | Adjuvant | Anti-S.flex Lung LPS IgA | | | |
|---|---|---|---|---|---|
| LPS (S.flex)-Proteosomes | None (saline) | 256 | 512 | 1024 | 2 |
| LPS (S.flex)-Proteosomes | Extrinsic SME | >2048 | >2048 | >2048 | >2048 |

Example 15

Oral (intragastric) Immunization of Mice with Lipopolysaccharide (LPS) Antigen from S. flex Complexed to Proteosomes Adjuvanted with Extrinsic-SME BALB/c mice (5 animals/group) were immunized orally (intragastrically) with 100 μg does of LPS complexed to proteosomes and adjuvanted with extrinsic SME. As shown in Table 5, the SME adjuvant formulation was able to induce higher anti-S. flex LPS intestinal IgA titers, compared to the free antigen.

TABLE 5

Induction of mucosal immunity after oral (intragastric) immunization of Balb/C mice with LPS-complexed to proteosomes as a free antigen or adjuvanted with extrinsic-SME

| Antigen | Adjuvant | Anti S.flex LPS intestinal IgA |
|---|---|---|
| LPS (S.flex)-Proteosomes | None | 74 |
| LPS (S.flex)-Proteosomes | Extrinsic-SME | 169 |

Example 16

Protection Against Systemic Challenge with SEB by SEB Toxoid Vaccines Formulated with SME Adjuvant Administered Parenterally or Intranasally Mice immunized parenterally (Table 6) or intranasally (Table 7) with Staphylococcus Enterotoxin B in mice immunized with SEB Toxoid-F vaccines formulated with SME or proteosomes were significantly protected against systemic SEB challenge (100 μg toxin).

TABLE 6

Correlation of anti-SEB serum IgG titers obtained after parenteral (i.m.) immunization (50 μg SEB-Toxoid F) with protection against systemic challenge with 100 μg SEB ion CD-1 mice

| Antigen | Adjuvant | Anti-SEB IgG | died/total | Survival |
|---|---|---|---|---|
| control | none | 0 | 10/18 | 44% |
| SEB-tox F | none | 3,200 | 3/5 | 40% |
| SEB-tox F | alum | 51,200 | 4/5 | 20% |
| SEB-tox F | SME-Extrinsic | 204,800 | 0/5 | 100% |
| SEB-tox F | SME-Intrinsic | 204,800 | 0/4 | 100% |

TABLE 7

Correlation of anti-SEB serum IgG titers with protection against systemic (im) challenge with 100 μg SEB in D-galactosamine-sensitized inbred (Balb/C) mice: effect of proteosomes and SME on efficacy of intranasal immunization with formalinized (Toxoid-F) SEB vaccines

| Vaccine | Adjuvant | Anti-SEB IgG serum titer | SED challenge results | |
|---|---|---|---|---|
| | | | #died/#total | Survived |
| None | None | <50- | 12/12 | 0% |
| Toxoid-F | SME | 51,200 | 4/7 | 40% |
| Toxoid F-Proteosomes | None | 409,600 | 2/5 | 60% |

The data in Table 6 show a very good correlation between the anti-SEB serum IgG titers obtained after intramuscular immunization of CD-1 mice with protection against systemic challenge with 100 μg of SEB. In the groups immunized with either extrinsic or intrinsic SME-SEB Toxoid F vaccines, the survival was 100% while for animals immunized with free antigen or alum-adjuvanted vaccine the survival was 0 and 40%, respectively.

Table 7 shows similar data for BALB/c mice immunized intranasally with SEB-Toxoid F alone or complexed to proteosomes in SME adjuvant or as free antigen.

Example 17

Enhanced Murine Immunogenicity of gp 160 HIV Antigen Incorporated in SME Adjuvants Either Intrinsically or Extrinsically The antigens used were gp 160 alone or gp 160 complexed to meningococcal outer membrane proteosomes. These antigens were formulated with SME either intrinsically or extrinsically and compared to the gp 160 used without an adjuvant, as described in Examples 1–4. Mice (5 animals/group) were immunized three times at 3–4 week intervals. Sera, obtained after 2 and 3 immunizations were analyzed for specific anti-gp 160 peptide IgG responses by quantitative Western blot techniques using seven specific HIV epitopes as the detecting antigens. As shown in Table 8a, both intrinsic and extrinsic formulations of SME were effective in enhancing immunity to several gp160 epitopes.

gens were formulated with SME either intrinsically or extrinsically and compared to gp160-alum, gp160-proteosomes, and gp160-proteosomes-alum formulations. Rabbits (4 animals/group) were immunized parenterally four times at different intervals. Sera, obtained after second, third and fourth immunizations were analyzed by for specific anti-gp160 peptide IgG responses by quantitative Eastern blot techniques using seven specific HIV epitopes as the detecting antigens. As shown in Table 8b, intrinsic formulations with SME with or without proteosomes were effective in enhancing immunity to several gp160 epitopes and even gp160 formulated with only an SEM-intrinsic preparation was as good as or better than gp160 formulated with alum, a known adjuvant currently used in people.

TABLE 8a

Sub-Micron Emulsions Enhance the Immunogenicity of Proteins alone or Protein-Proteosomes Complexes in Mice

| | | EPITOPES | | | | | | |
|---|---|---|---|---|---|---|---|---|
| Antigen | Adjuvant | C1 48–128 | C21E 254–274 | C3 342–405 | CKen 735–752 | C41 579–605 | C448 453–518 | V3 290–338 |
| | | Conserved areas of gp120 | | | gp40 areas of gp160 | | | variable loop |
| After 2 Immunizations | | | | | | | | |
| gp160 | none | 1 | 157,447 | 1 | 1 | 73,089 | 397,458 | 32,979 |
| gp160 | SME-intrinsic | 131,848 | 36,805 | 1 | 1 | 39,357 | 123,000 | 1 |
| gp160 | SME-extrinsic | 111,102 | 215,056 | 1 | 88,089 | 76,348 | 596,159 | 1 |
| gp160-proteosomes | none | 325,008 | 870,970 | 1 | 48,437 | 65,787 | 994,290 | 17,758 |
| gp160-proteosomes | SME-intrinsic | 1,772,367 | 1,237,152 | 162,326 | 1 | 161,763 | 411,147 | 1 |
| gp160-proteosomes | SME-extrinsic | 678,516 | 254,246 | 17,205 | 1 | 224,494 | 566,667 | 18,260 |
| After 3 Immunizations | | | | | | | | |
| gp160 | none | 354,732 | 350,071 | 1 | 13,879 | 183,047 | 535,709 | 62,257 |
| gp160 | SME-intrinsic | 131,211 | 186,281 | 1 | 2,807 | 119,449 | 130,965 | 1 |
| gp160 | SME-extrinsic | 241,500 | 382,106 | 1 | 56,308 | 105,334 | 551,054 | 46,416 |
| gp160-proteosomes | none | 576,316 | 617,847 | 1 | 149,657 | 346,582 | 922,360 | 416,493 |
| gp160-proteosomes | SME-intrinsic | 2,423,815 | 1,201,061 | 196,191 | 6,196 | 310,867 | 873,932 | 61,281 |
| gp160-proteosomes | SME-extrinsic | 88,454 | 584,250 | 4,298 | 19,432 | 64,524 | 301,775 | 132,800 |

TABLE 8b

Sub-Micron Emulsions Enhance the immunogenicity of Proteins alone in Rabbits

Data From Rabbit Immunogenicity

| | | | | | | | | |
|---|---|---|---|---|---|---|---|---|
| After 2 Immunizations | | | | | | | | |
| gp160 | alum | 92,402 | 63,382 | 3,288 | 35,913 | 29,721 | 22,150 | 10,183 |
| gp160 | SME-intrinsic | 95,403 | 84,672 | 27,840 | 50,221 | 103,119 | 94,622 | 88,896 |
| gp160 | SME-extrinsic | 126,521 | 143,598 | 6,243 | 2,604 | 86,541 | 69,847 | 44,426 |
| After 3 Immunizations | | | | | | | | |
| gp160-proteosomes | alum | 56,202 | 78,323 | 4,281 | 17,380 | 24,368 | 7,320 | 7,623 |
| gp160-proteosomes | SME-intrinsic | 36,980 | 13,608 | 5,339 | 6,333 | 21,318 | 36,369 | 54,347 |
| gp160-proteosomes | SME-extrinsic | 111,852 | 90,717 | 12,986 | 10,229 | 77,818 | 68,167 | 54,176 |

Note that the strongest and broadest anti-HIV responses were obtained with the intrinsic formulation using gp 160-proteosomes as the antigen (rows 5 and 11 in Table 8a).

Example 18

Figure 4:
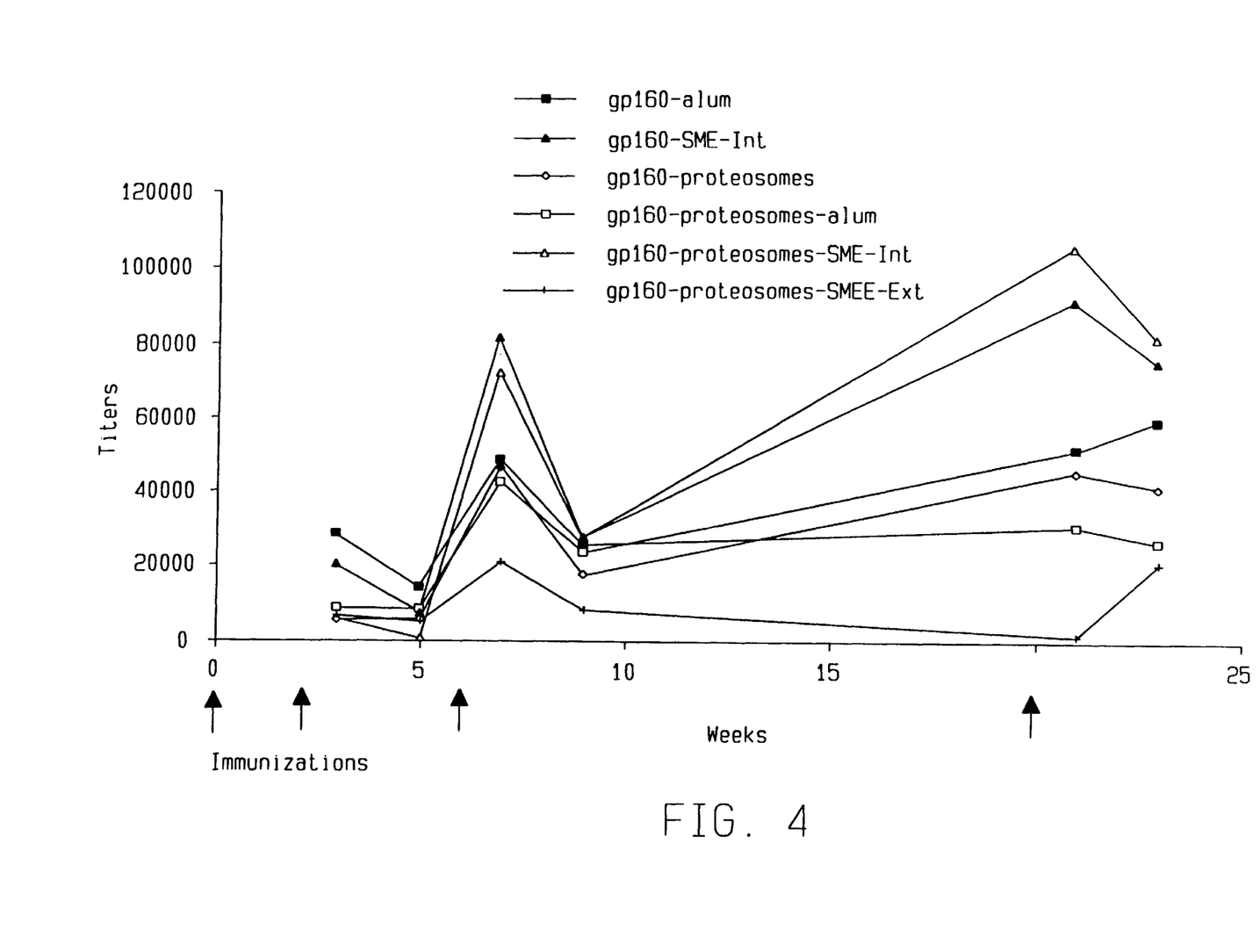
FIG. 4 shows the anti gp160 IgG antibody rabbit titers obtained after parenteral immunization with gp160 formulated in alum, proteosomes or SME adjuvants.
Figure 5:
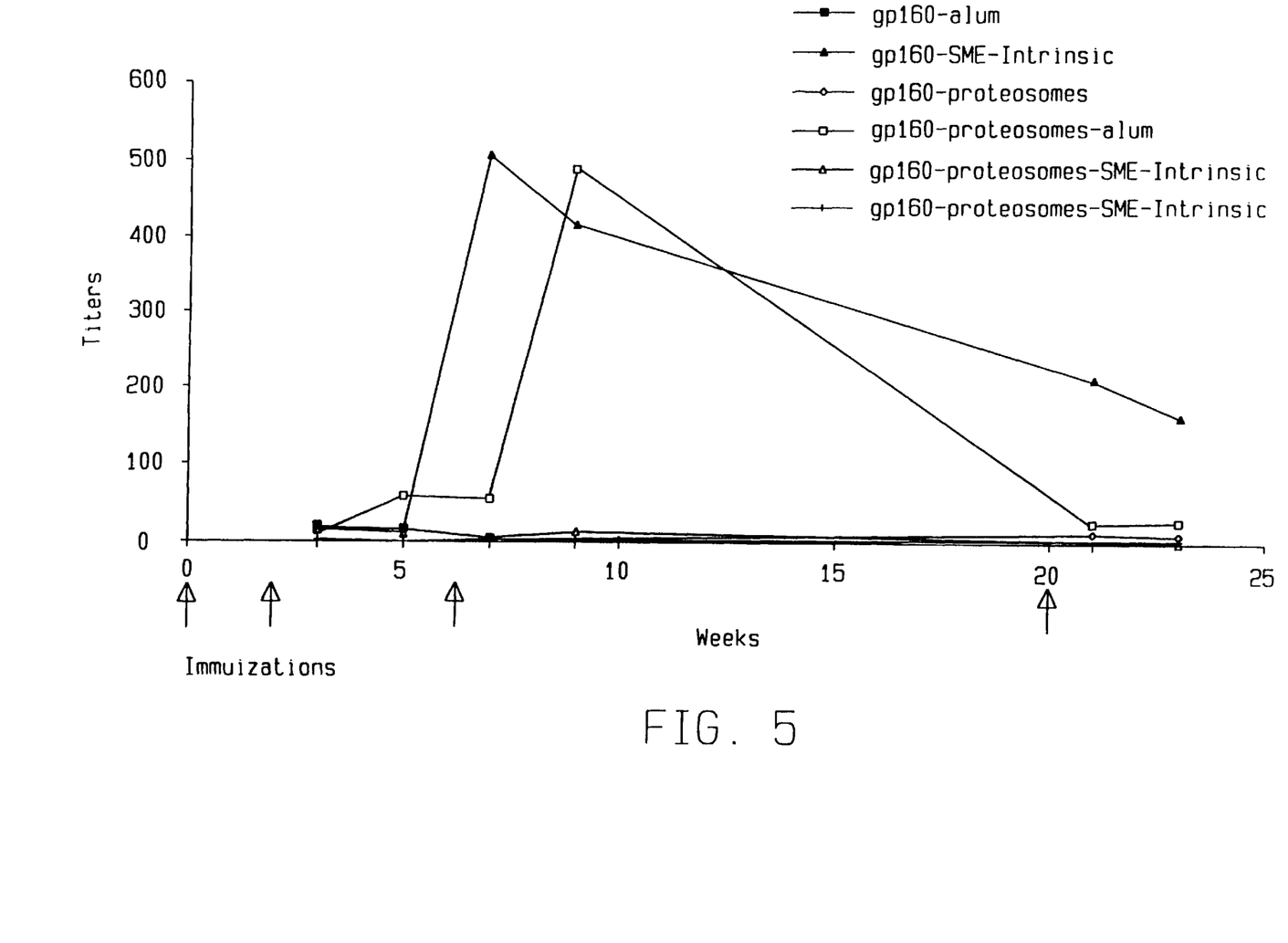
FIG. 5 shows the specific anti-Alex 10 (V3 loop) rabbit IgG titers obtained after parenteral immunization with gp160 formulated in alum, proteosomes or SME adjuvants.

Enhanced Lapine Immunogenicity of gp160 HIV Antigen Free or Complexed to Proteosomes Formulated in SME Vaccine Adjuvants The antigens used were gp160 alone or gp160 complexed to meningococcal outer membrane proteosomes. These anti- Another analysis of the experiment showing adjuvant effects of SME with gp160 vaccines in rabbits in which the antigens used were gp160 alone or gp160 complexed to meningococcal outer membrane proteosomes is shown in FIGS. 4 and 5. These antigens were formulated with SME either intrinsically or extrinsically and compared to gp160-alum, gp160-proteosomes, and gp160-proteosomes-alum formulations. Rabbits (4 animals per groups) were immunized parenterally four times at different intervals. Sera, obtained after second, third and fourth immunizations were analyzed by ELISA techniques using several specific HIV epitopes as the detecting antigens. As shown in FIG. 4, intrinsic formulations with SME with or without proteosomes were effective in enhancing immunity to several gp160 epitopes.

Among the six groups tested, the intrinsic-SME vaccine formulation containing the gp160 antigen in the absence of alum, was the most effective vaccine eliciting the high antibody titers with improved and extended immunogenicity against several selected gp 160 epitopes compared to the standard alum-adjuvanted vaccine actually in clinical trials.

More importantly, the SME-intrinsic formulations of gp160 were able to induce IgG antibodies against the V3 loop epitope of the gp160 molecule (FIG. 5 and Table 8b), the site of the principal neutralizing determinant which blocks binding to CD4 (the main cellular receptor for HIV). Since the standard alum-adjuvanted formulation did not generate antibodies against the V3 peptide domain, the additional epitope recognition and enhanced total immunogenicity of SME-intrinsic adjuvant is considered to be a very significant achievement.

These data are encouraging for the development of enhanced subunit formulations of gp160 vaccines for HIV vaccine therapy.

Example 19

Immunogenicity of Leishmania Glycoproteins Formulated in Extrinsic-SME Adjuvant either with or without Proteosomes The gene for a surface protein antigen of *Leishmania major* gp63, has been cloned and sequenced. This protein, recombinantly expressed in live Salmonella, or given in a sub-unit vaccine as either the purified native gp63 or selected gp63 peptides (Jardim A., Alexander J., Teh S., Ou D, Olafson R. W. 1990. J. Exp. Med. 172: 645), has recently been shown to limit the extent to lesion development in murein models of cutaneous leishmaniasis when given with certain adjuvants. These results suggest that a vaccine to protect humans against leishmaniasis composed of defined purified components is a realistic goal. The sub-unit vaccines were effective, however, only when administered with adjuvants containing *Corynebacterium parvum* (CPV) and poloxamer 407. Other adjuvants (Complete Freund's Adjuvant, CFA), or lack of adjuvant exacerbated disease.

Major success was achieved with the discovery that subcutaneous immunization with one small gp63 peptide covalently conjugated to lauryl-cysteine protected against sever Leishmania cutaneous lesions with reduction of lesions in three separate experiments.

The objective in the present example was to demonstrate immunogenicity and efficacy of an SME-adjuvanted lipopeptide vaccine to protect against severe morbidity of cutaneous leishmaniasis in murein models.

TABLE 9

Effect of immunization with LC-467 Leishmania lipopeptide formulated in SME adjuvant either with or without proteosomes on lesion size

| Formulation | % decrease on lesion size from Control in CBA |
|---|---|
| LC-467-proteosomes | 52 |
| LC-467-Extrinsic SME | 90 |
| LC-467-proteosomes-Extrinsic SME | 90 |

The antigen used were lipopeptides obtained from the major glycoprotein of the Leishmania parasite. The peptides (denoted 457 and 154) were covalently attached to lauryl cysteine to serve as the hydrophobic foot. The vaccine was prepared by gentle mixing of the antigens at room temperature with plain extrinsic-SME for 15 min.

Two animal models were used: (1) CBA mouse, model similar to human cutaneous disease; and (2) BALB/c mice, model similar to visceral Leishmania which is lethal if not treated.

The immunization protocol included two injections of the animals (8 mice/group) at weeks 0 and 3 with the experimental vaccines (50 µg peptide/mouse). At week 6 the mice were infected with live Leishmania parasites and the lesion size as function of time was measured and compared. The results were expressed as % decrease from control (PBS injection). Different vaccine formulations containing SME with or without proteosomes were tested. Appropriate control formulations were used.

All the formulations tested containing the 154 glycopeptide had no effect on lesion size, even if this vaccine contained proteosomes, SME or their combination. However, when the LC-467-glycopeptide was used, up to 90% decrease in lesion size was obtained by incorporation of the lipopeptide in SME, even in the absence of proteosomes (Table 8).

Since there is considerable homology among Leishmania strains, this peptide may have wide application in ameliorating lesions caused by other forms of Leishmania.

Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. A vaccine adjuvant composition of an oil-in-water submicron emulsion consisting essentially of about 0.5 to 50% of a first component of an oil, about 0.1 to 10% of a second component of an emulsifier, wherein the emulsifier is a phospholipid compound or a mixture of phospholipids selected from the group consisting of phosphatidylcholine, phosphatidylethanolamine, phosphatidylserine, phosphatidylinositol, phosphatidylglycerol, phosphatidic acid, sphingomyelin and cardiolipin, about 0.05 to 5% of a non-ionic surfactant, about 0.00001, to 1% of an immunogen, and an aqueous continuous phase, said submicron emulsion having a mean droplet size in the range of between about 0.03 and 0.5 µm, which composition is substantially free of added amounts of muramyl peptides or their lipophilic derivatives.

2. The emulsion of claim 1 wherein said mean droplet size is between about 0.05 and 0.2 µm.

3. The emulsion of claim 1, wherein said first component is selected from the group consisting of a medium chain triglyceride oil, a vegetable oil and mixtures thereof.

4. The emulsion of claim 3 wherein said first component is present in an amount of about 1 to 20%.

5. The emulsion of claim 1 wherein said emulsifier is present in an amount of about 0.2 to 5%.

6. The emulsion of claim 1 wherein said surfactant is selected from the group consisting of fatty alcohols, polyethylene glycol esters of fatty acids, polyethoxylated fatty acid esters, polyethoxylated fatty alcohol ethers and polyethoxylated alkylphenyl ethers.

7. The emulsion of claim 1 wherein said surfactant is an alkylene oxide condensate of an organic compound having one or more hydroxyl groups.

8. The emulsion of claim 7 wherein said non-ionic surfactant is present in an amount of about 0.1 to 5%.

9. The emulsion of claim 1 wherein said first component is present in an amount of about 1 to 20%, and the second component and the non-ionic surfactant are each present in an amount of about 0.1 to 2%.

10. The composition of claim 1 wherein said immunogen is selected from the group consisting of hydrophilic, lipophilic and amphiphilic immunogens.

11. The composition of claim 1 wherein said immunogen is selected from the group consisting of native, recombinant and synthetic peptides, proteins and glycoproteins derived from a source selected from the group consisting of bacteria, viruses and parasites.

12. The composition of claim 11 wherein said immunogen is the gp160 envelope protein of the HIV virus, or a fragment thereof.

13. The composition of claim 11 wherein said immunogen is the surface glycoprotein of a Leishmania parasite or a fragment thereof.

14. The composition of claim 13 wherein said surface glycoprotein or peptide is covalently conjugated to a hydrophobic foot.

15. The composition of claim 14 wherein said hydrophobic foot is lauryl-cysteine.

16. The composition of claim 1 wherein said immunogen is a protein toxoid.

17. The composition of claim 16 wherein said immunogen is Staphylococcus Enterotoxin B toxoid.

18. The composition of claim 1 wherein said immunogen is selected from the group consisting of an oligosaccharide, a polysaccharide and a lipopolysaccharide.

19. The composition of claim 18 wherein said immunogen is a lipopolysaccharide from *Shigella flexneri*.

20. The composition of claim 1 wherein said immunogen is completed to proteosomes.

21. A method for preparing the composition of claim 1 by an intrinsic procedure, which comprises adding the immunogen to the oil phase before emulsification of the water and oil phases.

22. A method for preparing the composition of claim 1 by an intrinsic procedure, which comprises adding the immunogen to the water phase before emulsification of water and oil phases.

23. A method for preparing the composition of claim 1 by an extrinsic procedure, which comprises preparing a submicron emulsion from the oil, surfactant and emulsifier components, and adding the immunogen externally by mixing it with the previously prepared submicron emulsion.

24. A method for providing enhanced immunogenicity in a subject which comprises administering the composition of claim 1, to the subject to introduce the immunogen therein.

25. The method of claim 24 which further comprises administering the composition parenterally, orally, intranasally or topically to the subject.

* * * * *